United States Patent [19]

Papadofrangakis et al.

[11] 4,182,173
[45] Jan. 8, 1980

[54] DUPLEX ULTRASONIC IMAGING SYSTEM WITH REPETITIVE EXCITATION OF COMMON TRANSDUCER IN DOPPLER MODALITY

[75] Inventors: Emmanuel Papadofrangakis, Schenectady, N.Y.; John A. Fakiris, Holly Hill, Fla.; William E. Engeler, Scotia, N.Y.

[73] Assignee: General Electric Company, Schenectady, N.Y.

[21] Appl. No.: 936,115

[22] Filed: Aug. 23, 1978

[51] Int. Cl.² .............................................. G01N 29/00
[52] U.S. Cl. ..................... 73/194 A; 73/641; 128/663
[58] Field of Search .................. 73/194 A, 592, 641, 73/633; 128/2 V, 2.05 F, 2.05 Z; 340/1 R

[56] References Cited
U.S. PATENT DOCUMENTS

| | | | |
|---|---|---|---|
| 3,939,707 | 2/1976 | Kossoff | 73/194 A |
| 4,097,835 | 6/1978 | Green | 73/641 X |

OTHER PUBLICATIONS

Coghlan, B. A., Directional Doppler. . . . Velocities from Ultrasound in Med. & Biol., vol. 2, pp. 181-188, Pergamon Press, 1976, Gt. Britain.

*Primary Examiner*—Jerry W. Myracle
*Attorney, Agent, or Firm*—Donald R. Campbell; Joseph T. Cohen; Marvin Snyder

[57] ABSTRACT

A duplex imaging system with a common transducer array for both modes of operation satisfies the conflicting bandwidth requirements by single impulse excitation of the transducer in B-scan imaging operation to generate a wide bandwidth ultrasound pulse and multiple impulse excitation at the emission frequency in Doppler mode operation to generate a narrow bandwidth ultrasound phase. The multiple impulse excitation has a variable repetition frequency depending on range to a sample volume and velocity of blood flow. A Doppler modality, in which the frequency shift of echoes caused by flow of blood is measured to derive the flow velocity, is incorporated into a sector scanner with little additional complexity.

14 Claims, 8 Drawing Figures

DUPLEX ULTRASONIC IMAGING SYSTEM WITH REPETITIVE EXCITATION OF COMMON TRANSDUCER IN DOPPLER MODALITY

BACKGROUND OF THE INVENTION

This invention relates to ultrasonic imaging systems with provision for measuring the velocity of liquid flow, and more particularly to satisfying the different bandwidth requirements of duplex systems having a common transducer array so as to realize optimum performance in either modality.

B-scan imaging systems for medical diagnostic examination produce a two-dimensional visual image of a planar slice through the human body, and are designed to offer optimum resolving power and contrast between tissue interfaces at dimensions comparable to the illuminating wavelengths. Ultrasound Doppler systems require information relating to blood flow velocity by detecting the frequency shifts imparted to ultrasound by reflection from moving red blood cells, and have the objective of providing adequate blood velocity discrimination over a certain range. Thus, B-scan images require broad band transducers for high resolution and Doppler systems on the other hand require narrow band transducers in order to provide accurate velocity readings. If the same transducer is to be used in a duplex system there is the problem of a conflicting bandwidth requirement.

Advances in imaging techniques have made a significant impact in the diagnosis of cardiovascular disease by improving medical science's ability to define structural disorders in the heart and great vessels. The ability would be greatly enhanced by developing sophisticated equipment for detecting abnormalities in blood flow in the arterial vessels and through the heart valves and cardiac chambers. Several methods for sensing blood flow parameters are known, but despite recent progress there still remains a need for a detection scheme that is safe, yields accurate data, and derives data rapidly enough to reflect variations occurring in the course of a heart cycle. The diagnostic value of such a scheme is vastly improved when combined with a suitable imaging technique so that the physician can determine the precise location in the blood stream from which data is reported. The use of a common transducer for B-scan and Doppler modes has advantages in the accuracy of orientation of the transmitted acoustic beam in the latter case and in system simplicity.

A currently available duplex ultrasound system utilizes a separate transducer for the B-scan and Doppler functions. In alternative implementations, involving a common transducer, the performance during imaging is compromised in order to obtain some frequency shift and velocity measuring facility. The object of this invention is to satisfy the conflicting transducer bandwidth requirements with minimum additional system complexity and without sacrifices in performance in either modality.

SUMMARY OF THE INVENTION

The requirement of a wide bandwith ultrasound pulse for B-scan imaging and a narrow bandwidth ultrasound pulse for detecting Doppler frequency shifts, which are imparted to ultrasound by backscattering from flowing blood or similar liquids, is resolved in a duplex system with a common transducer array by varying the transducer's electrical excitation. A single voltage impulse is applied to every selected transducer element with an element-to-element timing to generate a wide bandwidth pulse that is transmitted along a given scan line or beam direction. After scanning the region of the body or other object being examined and displaying the B-mode visual image, a sample volume is identified at which the velocity of blood flow is to be measured. Multiple voltage impulses with a frequency approximately equal to the required ultrasound emission center frequency are applied to selected array elements with an element-to-element timing to generate a narrow bandwidth ultrasound pulse that is transmitted along the chosen scan line intersecting the sample volume. Bandwidth is inversely proportional to the number of impulses, also referred to as shock or Dirac excitations, and the number of impulses per pulse repetition interval is usually constant and selected to be consistent with range and velocity resolution requirements. The pulse repetition frequency can be variable depending upon magnitude of velocity flow and range to the sample volume.

The preferred embodiment is a sector scan imaging system, and the Doppler mode is subsequent to the B-scan imaging and Doppler orientation mode and utilizes basically the same apparatus as for imaging with the exception that the focused and summed echo signals are fed to a spectrum analyzer or other Doppler processor in which the frequency shift of focused echoes with respect to the emission frequency spectrum of the transmitted pulse is measured. Means are provided to derive the velocity of blood flow from the frequency shift and for displaying the flow velocity. The variable pulse repetition frequency is coordinated with the Doppler display and has at least high and low settings. The pulser in the transmitter is controlled to deliver either single impulses to every selected transducer element or multiple impulses for Doppler operation. High performance is achieved in both modalities with a single transducer array.

DESCRIPTION OF THE PREFERRED EMBODIMENTS

Measurements of blood flow in the arteries and in the heart chambers have been found to be very useful in the diagnosis of cardiovascular disease, and the expectation is that the value of these measurements will dramatically increase as the measurement accuracy improves and as the blood flow measurements are combined with imaging techniques. Information concerning blood flow velocity can be obtained by measuring the Doppler frequency shifts imparted to ultrasound through backscattering from moving red blood cells. Backscattering is a specialized form of reflection and relates to scattering of sound waves in a direction approximately opposite to that of the incident waves due to reflection from particles of the medium traversed. Blood flow changes over the course of the heart cycle and physicians are therefore interested in the time variation of the red blood cell velocity distribution in a small insonified sample volume. In addition to estimating velocity, physicians are also interested in determining with accuracy the location in the blood stream from which velocity data is reported.

Figure 1:
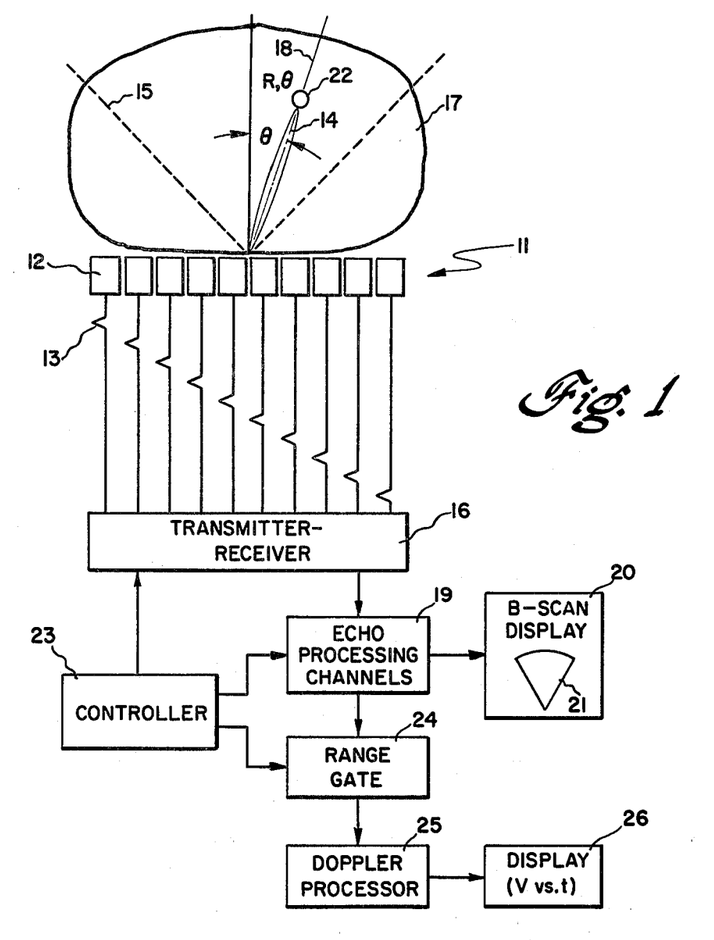
FIG. 1 is a simplified block diagram of a sector scan ultrasonic imager with which is incorporated a Doppler modality for blood velocity measurement.

Both needs are addressed by the Doppler modality of the duplex ultrasonic imaging system illustrated in the simplified block diagram of FIG. 1. A real time single-sector scanner has an incorporated Doppler mode of operation for blood flow velocity measurements capable of significantly improved performance as compared to prior art instruments. Use of the same array for imaging and velocity measurements is the key to increased accuracy. A different bandwidth requirement is imposed on the transmitted ultrasound pulse in the Doppler and imaging modes. Since the system concept is based on use of a common transducer array, the broad and narrow bandwidth requirements of the two modes are satisfied without compromising performance in either modality by implementing variable transducer excitation duration. In order to be able to adequately sample backscattered echoes from slow as well as fast moving red blood cells, it is desirable to have variable repetition intervals for this excitation. Before proceeding further, principles of beam formation and echo signal processing in steered beam imagers are reviewed.

Common linear transducer array 11 in FIG. 1 is comprised of a large number of piezoelectric transducer elements 12 which are energized by excitation pulses 13 in a linear time sequence to form an ultrasound beam 14 and direct the beam in a preselected azimuth direction to transmit a pulse of ultrasound. In order to steer the beam electronically to an angle $\theta$ degrees from the normal to the array longitudinal axis, a time delay increment is added successively to each signal as one moves down the array from one end to the other to exactly compensate for the propagation path time delay differences that exist under plane wave (Fraunhofer) conditions. By progressively changing the time delay between successive excitation pulses, the angle $\theta$ on one side of the normal is changed by increments, and to form a steered beam at the other side of the normal, the timing of excitation pulses 13 is reversed so that the right hand transducer is energized first and the left hand transducer is energized last. A total sector scan angle indicated by dashed lines 15 is approximately 60 degrees to 90 degrees. Echoes returning from targets in the direction of the transmitted beam arrive at the transducer elements at different times necessitating relative delaying of the received echo electrical signals by different amounts so that all the signals from a given point target are summed simultaneously by all elements of the array. The time delays of the individual echo signals are the same as during transmission to compensate for acoustic path propagation delay differences, and these are referred to as being steering time delays or simply steering delays. Every receiving channel also electronically and dynamically focuses the received echoes to compensate for the propagation path time delay differences from the focal point to the various individual array element positions. The receiving focus can be dynamically changed to track the range from which the echoes are being received during the echo reception period by a multistep approximation. The preferred embodiment of the sector scanner in FIG. 5 features fine and coarse step focusing, where fine focusing is achieved by using dynamically phased synchronous demodulation and coarse focusing is accomplished as in beam steering by channel-to-channel electronic signal delay differences. The demodulator subsystem uses in-phase and quadrature waveforms at the nominal center frequency of the transducer to translate the received signals in each channel to base band while preserving their phase. The relative phases of each channel are controlled by dynamically varying the phases of these waveforms in accordance with a predetermined schedule such that the phases of all receiver channels focus for scatterers at all ranges. Electronically variable delay lines provide the steering and focusing time delays. To effect coherent summation of the contributions from all receive elements, the delayed echo signals from the in-phase and quadrature receiving channels are fed to summing amplifiers at the output of which is a focused echo signal. Further processing of all the focused signals generates the raw display data.

There are two modes of operation of the duplex imager system for velocity measurements: (a) the B-scan imaging and Doppler orientation mode and (b) the Doppler processing and display mode. The latter modality is always subsequent to the former and the two are never simultaneous. During successive transmission periods of the B-scan mode, transmitter-receiver 16 (FIG. 1) generates a series of excitation impulses 13, one per transmitter element, with a time delay between successive impulses that is incremented from one transmission period to the next to thereby transmit pulses of ultrasound along many different scan lines covering the region of a body 17 being examined. Single impulse excitation of the transmitter array produces short duration, wide bandwidth ultrasound pulses. From this description, it is seen that an emitted ultrasound pulse can be directed along any chosen scan line, such as scan line 18, by properly selecting the order of element excitation and the time delay increments between pulsing the elements. During alternate reception periods, the received echo signals caused by energy echoing from various body structures and detected by receive elements in common array 11 are individually amplified and fed to echo processing receiving channels 19. The summed and focused echo signals may be post-processed to improve the image and are presented to a cathode ray tube or other B-scan display device 20. Sector-shaped image 21 is a two-dimensional picture of a planar slice through the body which is built up scan line by scan line as echo information is received and can be displayed in real time.

A physician observing the real time B-scan image now identifies a relatively small sample volume within the heart or closeby great arterial vessels through which the velocity of blood flow is to be measured. A suitable landmark on the image can delineate the Doppler examination region, such as means for illuminating the beam direction through the sample volume and an illuminated range cursor. For instance, assume that a sample volume 22 is being examined which is along scan line 18 at an angle θ to the normal and which has a range R. In the Doppler mode of operation the system controller 23 is set by the user such that narrow bandwidth pulses of ultrasound are transmitted only along the chosen scan line through the sample volume, and range gating is employed to sample echoes from the desired depth and detect velocity patterns at specific locations. Repetitive pulsing of the transmitter elements at a frequency equal to the required emission frequency causes the response bandwidth of the transducer to be narrowed. By an appropriate timing of the beginning of the multiple pulsing of each element (the time delay increments are the same as for single impulse excitation), the transmitted ultrasonic beam is steered to a certain direction or can be focused to a certain point in space. The received echoes originating from the R,θ location of sample volume 22 are processed through receiver 16 and receiving channels 19, one per unit receive element, in exactly the same manner as for B-scan imaging to electronically steer and dynamically focus the echo signals, with the exception that the focused signals are sampled at a specific time after each transducer excitation interval which corresponds to the time taken for the ultrasonic signal to return to the transducer from range R. A range gate 24 is opened by controller 23 at the appropriate time for a relatively short interval and the extracted samples are passed to a Doppler processor 25.

After a number of narrow bandwidth pulse transmissions and echo receptions, the focused echo signal samples are analyzed to measure the Doppler frequency shift caused by blood flow in the sample volume and to derive the velocity of blood flow from the frequency shift. Doppler processor 25 is a spectrum analyzer and is preferably a digital Fast Fourier Transform (FFT) processor. Full spectral analysis is a powerful method using the entire power spectrum of Doppler shifted components that correspond to the red blood cell velocity distribution in the sample volume. The power spectrum contains all the available information concerning the flow of blood through the transducer beam. The output spectral components can be averaged in a mathematically correct way to obtain accurate mean frequency estimates. Knowledge of the speed of sound in tissue and emitted ultrasound frequency provides the additional parameters necessary for a mean velocity reading. Unidirectional velocity measurement or bidirectional velocity measurement are both possible, and either the distribution of blood velocities or the mean velocity can be displayed. Doppler mode display device 26 has an output reading of velocity vs. time, and a cardiac ECG signal may also be displayed to provide a time reference for events occurring during the course of a heart cycle.

Figure 2:
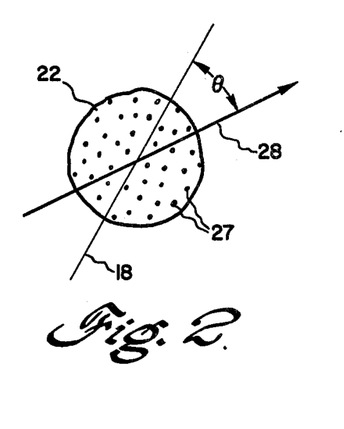
FIGS. 2 and 3 are enlarged views of a sample volume of blood showing in FIG. 2 a velocity vector at an angle $\theta$ to the transmitted acoustic beam and in FIG. 3 a sample volume with turbulent flow.
Figure 3:
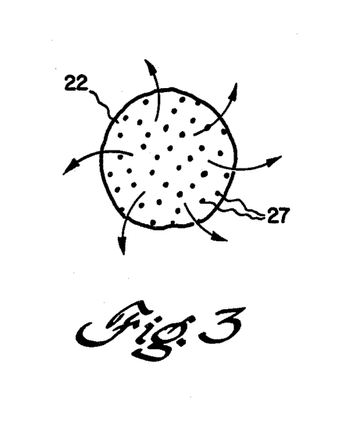

FIG. 2 is an enlarged view of sample volume 22 and of the red blood cells 27 in the blood stream which are very small (about 8 microns in diameter) as compared to the ultrasound wavelength. The red blood cells move with a certain mean velocity indicated by arrow 28 that is at an angle θ to the direction of the incident energy along scan line 18. The backscattered echoes from the red blood cells are frequency shifted by an amount proportional to the frequency of the incident wave and the velocity of blood flow. Movement of red blood cells through the sample volume toward the transducer array compresses the wavelength of the reflected wave, increasing the frequency; movement of red blood cells away from the transducer array lengthens the wavelength of the reflected wave, decreasing the frequency. The instrument measures only the component of mean velocity 28 in the direction of the transmitted ultrasound beam defined by scan line 18. The formula relating the Doppler frequency shift and velocity is $$\Delta f = \frac{2f_o v \cos \theta}{c} \quad (1)$$

where $\Delta f$=frequency shift, $f_o$=ultrasound emission frequency, v=mean velocity of blood flow, and c=speed of sound tissue (1450 m/sec). The range of blood velocities for humans is known and Doppler shifts are in the audio spectrum of about 0.2 KHz to 8 Khz. The ultrasound emission frequency for cardiac scanning is in the order of 2–5 MHz. The red blood cell population of sample volume 22 is constantly changing and it is necessary to get a number of samples of frequency shifted echoes in order to calculate an accurate value of velocity. Another factor is that blood flow may be turbulent as shown in FIG. 3 and a broad distribution of velocities may be present in the sample volume. The velocity vectors are, in general, oriented in many directions. The present duplex system acquires 16 samples in the Doppler mode for each velocity determination, i.e., there are sixteen ultrasound pulse transmissions and sixteen in-phase and sixteen quadrature focused echo signals are generated and gated to the Doppler processor, but this number of samples is not essential.

Red blood cells 27 moving past sample volume 22 back-scatter ultrasonic energy containing a spectrum of Doppler frequencies. These correspond to the distribution of velocities present in the sample region and mean velocity can be calculated by averaging the components of the distribution. In cardiology applications, one wishes to position the sound beam into a particular valve orifice or ventricular chamber and detect velocity patterns at these specific locations. Velocity at a specific point can more accurately be obtained by making the dimensions of the sample volume as small as possible. The sample volume is spherical or tear-drop shaped with a diameter of approximately 2 mm. Flow patterns in specific points in the heart may be complex, particularly if the flow is turbulent. Sampling over an extended region would tend to average out velocity components and result in a confusing pattern at the display.

Figure 4:
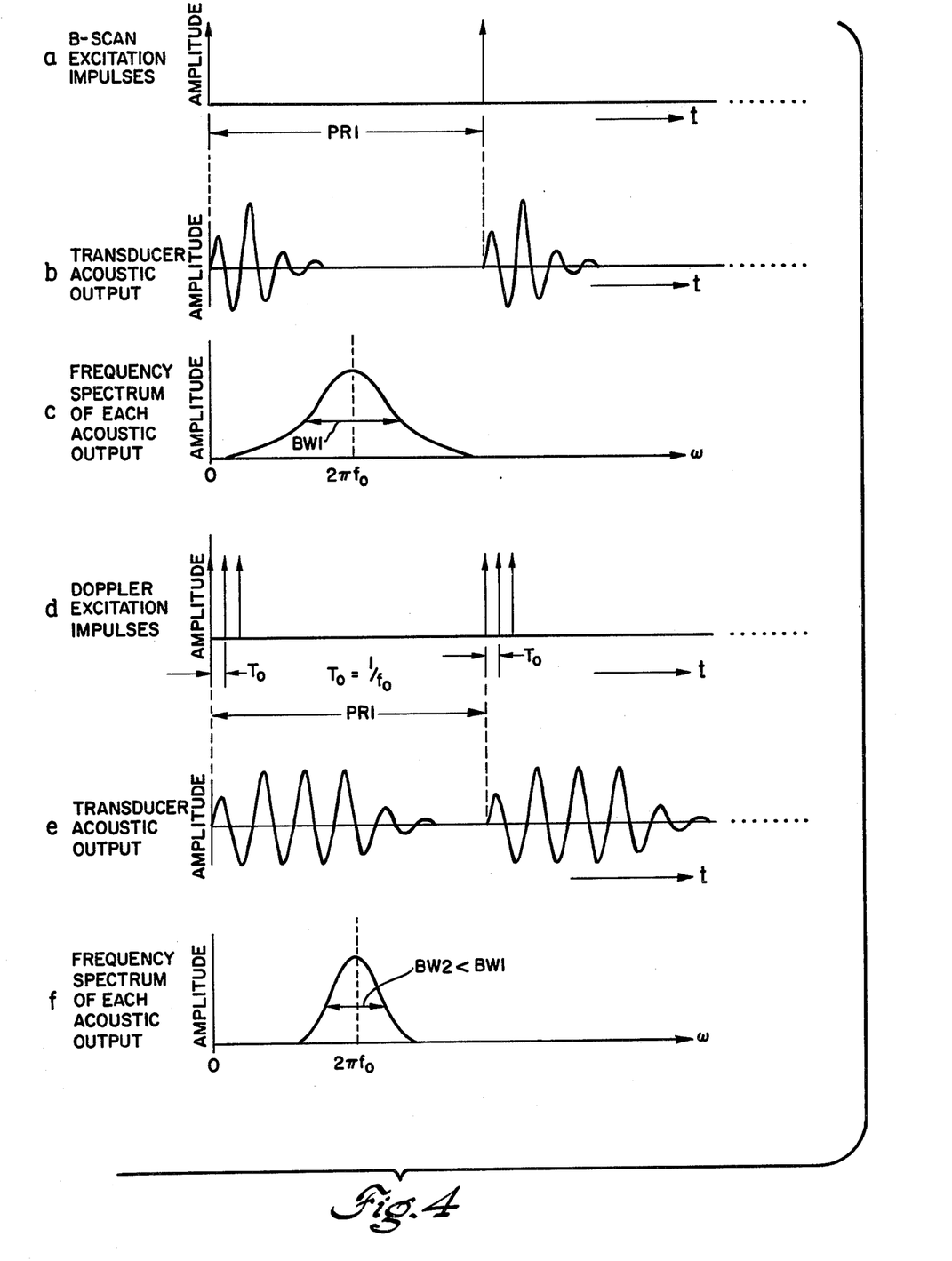
FIGS. 4a–4f are a series of waveform diagrams of the B-scan transducer excitation impulses, acoustic output, and broadband frequency spectrum, and a similar series for the Doppler mode using multiple impulses to produce a long duration acoustic pulse with a narrow bandwidth.

The performance objective in the B-scan imaging mode is to offer optimum resolving power and contrast between tissue interfaces of dimensions comparable to the illuminating wavelengths. To meet this objective, emitted ultrasound signals need to be short in duration, and such signals can be provided by inherently broadband transducers excited by a short electrical impulse. Ultrasound Doppler systems on the other hand require relatively narrow band transducers in order to provide adequate velocity discrimination, and fine spectral or velocity discrimination requires a longer duration ultrasound pulse. The conflicting transducer bandwidth requirements are satisfied in a duplex system with a common transducer array by providing variable excitation duration. Common transducer array 11 (FIG. 1) has wide bandwidth elements 12, and the maximum bandwidth allowed by the material properties of the selected piezoelectric can be obtained by a Dirac function excitation. Dirac excitation is also referred to as shock excitation or impulse excitation and the latter term is used here. For B-scan operation, a single excitation impulse (FIG. 4a) is applied to every transmitter element in each ultrasound pulse repetition interval (PRI). The acoustic output of the transducer (FIG. 4b) is a short duration emitted ultrasound pulse capable of good axial or range resolution which has a relatively wide bandwidth (FIG. 4c). A vertical dashed line designates the emission center frequency. For Doppler mode operation the transducer element is excited by multiple pulse excitations (FIG. 4d) in every PRI which are repeated at the required emission frequency. The impulse period $T_o$ is inversely proportional to the emission center frequency $f_c$. The transducer acoustic output (FIG. 4e) is a longer duration emitted ultrasound pulse having a relatively narrow bandwidth (FIG. 4f) which is inversely proportional to the number of impulse excitations in the PRI. This technique of multiple pulsing to generate a narrow bandwidth ultrasound pulse is valid for a single transducer element and also for an array of elements. With proper element-to-element timing of the multiple pulses for each element, the transmitted beam can be steered to a chosen beam direction or focused at a given focal point.

Another feature of the Doppler modality transducer excitation is variable repetition intervals for the multiple excitation in order to be able to adequately sample, at various ranges, backscattered echoes from slow as well as fast moving blood cells. Variable ultrasound pulse repetition frequency is not essential to the invention as most broadly defined but is required in the preferred embodiment being described having a Doppler modality incorporated into a real time sector scanner. The requirement of a variable excitation repetition interval is best explained mathematically and is as follows. Pulse Doppler relies on detecting the frequency of variation in time of echo samples obtained during the course of several transmissions. Sampled data processes obey Nyquist's sampling theorem, which simply states that all available information can be extracted from a repetitive string of data provided the data is sampled at a rate at least twice the highest frequency content of the information. In the pulsed Doppler case this means that all information can be extracted from our echo samples if we arrange to obtain at least two samples per period of maximum frequency. In other words, the highest Doppler frequency shift $f_{Dmax}$ that any processor can detect is given by half the pulse repetition frequency (PRF) or sampling frequency.

$$f_{Dmax} = \frac{PRF}{2} \quad (2)$$

If N samples of data are obtained before processing, the spectral resolution of the processor is $$\Delta F = \frac{PRF}{N} \quad (3)$$

From equation (1) this translates in a velocity resolution given by $$\Delta v = \Delta F \frac{c}{2f_o \cos\theta} \quad (4)$$

Apart from velocity, the system must be capable of providing range resolution, and the unambiguous range of the system is again dependent on PRF. If $R_{max}$ is the unambiguous range required and c is the velocity of sound in tissue, ultrasonic transmissions must be repeated at a period equal to $2R_{max}/c$, or in other words the system PRF must be $$PRF = \frac{c}{2R_{max}} \quad (5)$$

Blood velocity in the arterial circulatory system varies between values of a few centimeters/sec to about 2 meters/sec. In order to design a processor capable of resolving velocities in this range, one has to determine the PRF and the number of samples N to be processed before an output is reported. Assume that N=16 (the question of N will be returned to) and examine the PRF choice. For emission frequencies of 3.5 MHz and 5 MHz, with the PRF chosen to be 4 KHz, 8 KHz, and 16 KHz, it can be shown that $R_{max}$ decreases in each case from about 19 cm to 4.8 cm, the spectral resolution $\Delta F$ changes in each case from 250 Hz to 1000 Hz, and $\Delta v$ increases as the PRF increases. The high PRF of 16 KHz is desirable when velocity data changes rapidly, but at this frequency the unambiguous range is only 5 cm from the skin and the velocity resolution ($\Delta v$) is coarse. The latter difficulty could be overcome by increasing the number of samples N by a factor of four, but then the emitted ultrasound pulses would be of long duration and this adversely impacts the range resolution of the system. The solution is to provide variable PRF for Doppler mode operation. For high values of velocity flow in sample volumes at close ranges, detection is accomplished by using a 16 KHz PRF. The velocity resolution is relatively poor. Superior velocity resolution at low flow velocities and at long ranges is achieved by the 4 KHz PRF. To provide additional flexibility in the choice available to the user there is an intermediate setting of 8 KHz PRF. The chosen PRF (ultrasound pulse repetition frequency) values in the Doppler mode are considerably higher than those provided in imaging, and the transmitter subsystem is capable of providing appropriate excitation intervals for both modes of operation.

A mathematical justification and analysis of variable transducer excitation for the two modalities will now be given. The performance objective in the Doppler mode of operation is to attain unambiguous velocity measurements, and this translates into the requirement that if a single velocity is present in detection, the Doppler processor must report an output frequency in a single spectral cell. If a single velocity is present and broadband signals are transmitted, the highest Doppler shifted frequency to be detected is $$2(f_c + \frac{B}{2})\frac{v}{c}, \quad (6)$$

where $f_c$=emission center frequency, and B=emission bandwidth, and the lowest is $$2(f_c - \frac{B}{2})\frac{v}{c} \quad (7)$$

For unambiguous velocity measurement $$2(f_c + \frac{B}{2})\frac{v}{c} - 2(f_c - \frac{B}{2})\frac{v}{c} < \Delta F. \quad (8)$$

From equations (8) and (3), $$2B\frac{v}{c} < \frac{PRF}{N} \quad (9)$$

The worst case is when $v = v_{max}$ and therefore (9) can be written:

$$\frac{2Bv_{max}}{c} \leq \cdot \frac{PRF}{N} \quad (10)$$

The maximum velocity that can be detected is given by equations (1) and (2).

$$f_{Dmax} = \frac{2f_c v_{max}}{c} = \frac{PRF}{2} \quad (11)$$

From (11) $v_{max}/c = PRF/4f_c$ and substituting into (10) it is clear that for unambiguous velocity measurement the bandwidth of the emitted ultrasound pulse must be:

$$B \leq \frac{2f_c}{N} \quad (12)$$

and the transducer Q is then $$Q \geq \frac{N}{2} \quad (13)$$

Equations (12) and (13) give the trade-off already alluded to between velocity and range resolution. Increasing N, the number of samples, to obtain improvements in spectral resolution, results in higher values of Q, lower transmit signal bandwidth, and therefore, a reduction in range resolution, which is given by:

$$\Delta r = \frac{C}{2B} = \frac{Nc}{4f_c}. \quad (14)$$

The exemplary embodiment of the invention uses a value of N=16, that is, velocity information is extracted from 16 samples obtained one at a time from 16 consecutive ultrasound transmissions. The signal being sampled has a bandwidth B determined by the transducer bandwidth. From equation (13) it is concluded that in Doppler mode the emitted ultrasound signals must be at least eight wavelengths long. The number of multiple impulses repeated in each pulse repetition interval (FIG. 4d) at the required emission frequency or at the natural frequency of the transducer element, is also eight. A nominal value of eight shock excitations per PRI provides a signal duration compatible with velocity resolution requirements.

Figure 5:
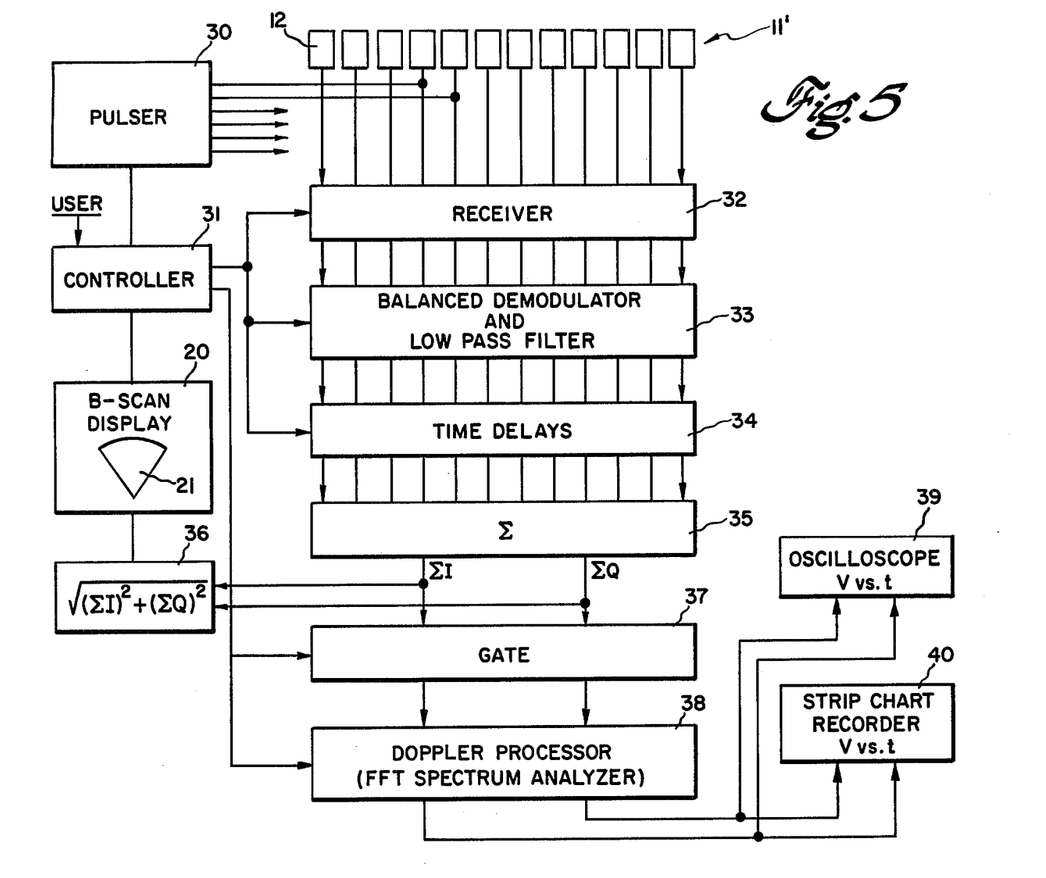
FIG. 5 is a simplified block diagram of the preferred embodiment of the duplex imaging system with a common transducer array for both modes.

The preferred embodiment of the invention depicted in somewhat greater detail in FIG. 5 is a real time single-sector ultrasound scanner into which is incorporated a Doppler modality for directional blood flow velocity measurement. Common linear transducer array 11' has a greater interelement spacing for receive than for transmit to yield a wide aperture system with low side lobe artifacts using a minimum number of relatively expensive receiver channels. The transmit array is at the center of a larger receive array (elements in the center may function dually as transmit and receive elements), and the transmit elements are associated with a pulser 30 capable of generating single impulses for B-scan operation, and multiple impulses for Doppler operation having a frequency approximately equal to the required emission center frequency. The relative element-to-element timing of the single or multiple impulses is such as to respectively transmit a broad bandwidth and narrow bandwidth pulse of ultrasound along a chosen scan line. The repetition frequency of multiple pulse excitation is variable and has high, intermediate, and low settings selected by a controller 31 with user inputs. The major components of the receiving channels, which feature the use of base band signal processing to achieve good lateral resolution while greatly reducing the required time delay accuracy and instead requiring more easily achieveable phase focusing accuracy, have as major components a receiver 32 for every channel, a balanced demodulator and low pass filter 33, a time delay device 34, and summers 35. The individual receiving channels have parallel I (in-phase) and Q (quadrature) processing channels in which the received echo signals are electronically steered and dynamically focused. Each signal is amplified and demodulated by a steady reference signal of a phase determined by the path length to the point under examination, and the output of each demodulator is low pass filtered to preserve the envelope and then delayed. In the situation where the path lengths differ sufficiently, a delay proportional to the path length difference is also provided before summing. This sum forms the in-phase or I output. Similarly, a summed quadrature or Q output is formed by demodulating the signals from the transducer by a set of reference signals, each 90° out of phase with the set of previous reference signals. Additionally, the outermost receiving channels are blanked progressively at shorter ranges to reduce the receive aperture and realize improved lateral resolution near the skin. For B-scan operation, the summed and focused I and Q signals are further processed at 36 to derive a resultant signal, obtained by squaring the I and Q signals, adding together these squared signals and taking the square root of the sum. The resultant is the video signal and it is postprocessed to improve the image before being fed to cathode ray tube 20 as the Z control or to control the electron beam intensity. The image is built up scan line by scan line as the transmitted beam direction is changed incrementally.

Further reviewing, Doppler orientation involves visual examination of B-scan image 21 by the physician or other operator to identify the sample volume 22 through which blood flow velocity is to be determined and select the scan line or beam direction $\theta$ and range R for the Doppler modality The R,$\theta$ coordinates the sample volume 22 are entered on controller 31 and are also illuminated on the screen of cathode ray tube 20.

Figure 6A:
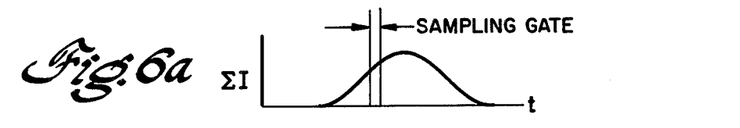
FIGS. 6a and 6b show the summed in-phase and quadrature focused echo signals input to the Doppler processor.
Figure 6B:
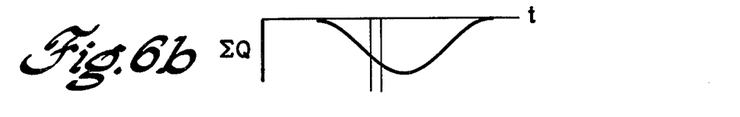

In the Doppler mode of operation the system insonifies only a selected direction $\theta$ and is in fact focused at range R. The repetition frequency of the multiple impulse excitation can be 4, 8 or 16 KHz and is entered by the operator. A narrow bandwidth pulse of ultrasound is generated and propagates along the chosen scan line intersecting the sample volume. During the course of a pulse repetition interval, three system parameters are varying in the receiving channels exactly as they do for B-scan imaging, these being the receive aperture width, the reference signal of the balanced demodulators, and the time delay between elements. The values of these three parameters are at the instant of Doppler sampling automatically those required to focus at range R, and although they vary during the course of a pulse repetition interval, they are always the same at the selected instance of sampling from one repetition interval to the next. Gate 37 is opened for a very short sampling interval (such as 0.1 microsecond) at a time after each transducer excitation such that only focused echo signals for range R are fed to Doppler processor 38, which is a 16-point digital FFT spectrum analyzer. Samples from sixteen consecutive transducer pulse repetition intervals are converted to digital form and stored in the Doppler subsystem memory prior to processing. Typical summed I and summed Q signals are shown in FIGS. 6a and 6b and contain a distribution of Doppler shifted frequencies. The I and Q focused signals, it is noted, are of opposite polarity, and the very short sampling gates are illustrated.

Figure 7:
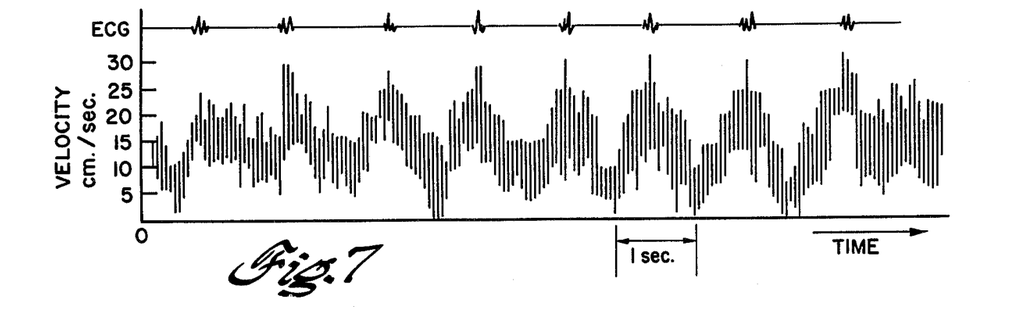
FIG. 7 is a typical velocity vs. time display for the Doppler mode.

At each instant in time, the Doppler processor reports the ultrasound power spectra backscattered from the sample volume. This corresponds to the velocity distribution in the sample volume; the distribution contains eight positive readings (forward flow) and eight negative readings (receding flow). The velocity components present in the sample volume may be averaged and a mean velocity reading displayed. Alternatively, the entire distribution can be displayed and this approach is preferred in situations of turbulent flow. Two displays are provided by the system for the velocity information. The sixteen Doppler frequencies are first displayed on an oscilloscope 39 so that the user can observe their variation in real time. A hard copy of the evolution of the velocity distribution with time is obtained by using a strip chart recorder 40. A typical plot of blood flow velocity vs. time is given in FIG. 7, and is multiplexed with an ECG signal to provide a time reference for events occurring in the course of a heart cycle. The velocity scale for strip chart recorder 40 is coordinated with the selection of pulse repetition frequency that the system will use. The selection procedure is to start with the maximum velocity, and therefore the maximum PRF, consistent with the selected range, and then decrease it in binary steps if the observed result is less than one-half cycle. This procedure avoids aliasing the Doppler velocity. Further information on the directional detection of blood flow velocities by synchronous demodulation of received echoes into quadrature components and subsequent processing by a digital Fourier Transform processor is given in concurrently filed application Ser. No. 936,111 by E. Papadofrangakis and W. E. Engeler.

A real time ultrasound imaging system which includes coherent demodulation of echo signals followed by time delay and coherent summation of the demodulated signals is described and claimed in allowed copending application Ser. No. 908,908 filed on May 24, 1978 by W. P. Engeler and J. J. Tiemann, now U.S. Pat. No. 4,155,260. Other aspects of the preferred embodiment of the duplex imaging system are explained in allowed Ser. No. 884,952 filed on Mar. 9, 1978, F. L. Lederman and J. J. Tiemann, "Transmit-Receive Transducer Array and Ultrasonic Imaging System"; and allowed Ser. No. 864,597 filed on Dec. 27, 1977, C. E. Thomas, "Dynamic Array Aperture and Focus Control for Ultrasonic Imaging System". All the foregoing patent applications are assigned to the same assignee as this invention.

The invention can be practiced with many different types of B-scan ultrasonic imagers including, but not limited to, rectilinear scanners and sector scanners whose details differ from those just described. All such duplex systems have a common transducer array and the different bandwidth requirements on the transmitted ultrasound pulse in the Doppler and imaging modes is satisfied while preserving optimum performance in both modes by implementing variable transducer excitation duration. An alternative to narrowing the bandwidth of the emitted ultrasound pulse for the Doppler modality is the use of an appropriate band pass filter. However, this alternative necessarily involves the loss of some signal. The approach described does not involve any signal rejection and from a signal-to-noise point of view is superior to the filter alternative.

While the invention has particularly shown and described with reference to preferred embodiments thereof, it will be understood by those skilled in the art that the foregoing and other changes in form and details may be made therein without departing from the spirit and scope of the invention.

The invention claimed is:

1. In a duplex ultrasonic imaging system having a common transducer array comprised of plural electroacoustic elements for transmitting and receiving pulses of ultrasound during a B-scan imaging mode and also during a subsequent Doppler mode in which the frequency shift of echoes relative to the ultrasound emission frequency spectrum caused by flow of blood or similar liquids in an insonified sample volume of the object being examined is measured to derive therefrom the flow velocity, the method of exciting said transducer array to vary the bandwidth of emitted ultrasound pulses which comprises in the B-scan modality applying a single impulse to every selected transducer element to generate a pulse of ultrasound with a broad bandwidth, and in the Doppler modality applying multiple impulses to every selected transducer element to generate a pulse of ultrasound with a narrow bandwidth, said multiple impulses having a frequency approximately equal to the ultrasound emission center frequency.

2. The method of claim 1 wherein the multiple impulses exciting every selected transducer element in the Doppler modality are repeated at a variable repetition frequency to thereby generate narrow bandwidth pulses of ultrasound at different rates.

3. The method of claim 2 wherein said variable repetition frequency has at least high and low settings selected in dependence upon the magnitude of flow velocity and range to the sample volume.

4. The method of claim 2 wherein the number of impulses per variable repetition interval exciting every selected transducer element is constant.

5. In a duplex ultrasonic imaging system having a common linear transducer array comprised of plural electroacoustic transducer elements for transmitting and receiving pulses of ultrasound during a B-scan imaging and Doppler orientation mode and also during a subsequent Doppler mode in which the frequency shift of echoes relative to the ultrasound emission frequency spectrum caused by flow of blood in an insonified sample volume of the subject being examined is measured to derive therefrom the flow velocity, the method of exciting said linear transducer array to vary the bandwidth of emitted ultrasound pulses which comprises in the B-scan modality applying a single voltage impulse to every selected transducer element with an element-to-element timing to generate a pulse of ultrasound with a broad bandwidth, and in the Doppler modality applying multiple voltage impulses to every selected transducer element with an element-to-element timing to generate a pulse of ultrasound with a narrow bandwidth inversely proportional to the number of impulses, said multiple impulses having a frequency approximately equal to the ultrasound emission center frequency.

6. The method of claim 5 wherein said multiple impulses exciting selected transducer elmeents are repeated at a preset but variable repetition frequency to thereby generate narrow bandwidth pulses of ultrasound at different rates.

7. The method of claim 6 wherein the number of impulses per pulse repetition interval in the Doppler mode is constant, and wherein the variable repetition frequency is selected in dependence upon the magnitude of flow velocity and range to the sample volume.

8. A method of diagnostic examination with a duplex ultrasonic imaging system having a common transducer array of electroacoustic elements for both a B-scan and Doppler orientation mode and a Doppler mode in which the velocity of blood flow is measured comprising the steps of
   applying a single impulse to selected array elements in time sequence to generate a wide bandwidth ultrasound pulse with a preselected emission center frequency that propagates along a given scan line,
   repeating the single impulse excitation of said array elements and sequentially transmitting ultrasound pulses along many scan lines at different angles to perform a sector scan of a region being examined, while alternately after every pulse transmission detecting received echoes and producing echo signals which are focused and summed and displayed as a visual image of the insonified region,
   choosing the scan line that intersects a sample volume through which the velocity of blood flow in to be measured,
   applying multiple impulses to each of said array elements with an element-to-element timing to generate a narrow bandwidth ultrasound pulse that is transmitted along the chosen scan line through the sample volume, said multiple impulses having a frequency approximately equal to said emission center frequency,
   repeating the multiple impulse excitation of said array elements to generate narrow bandwidth pulses that are transmitted along the chosen scan line, while alternately after every pulse transmission detecting received echos and focusing and summing the echo signals,
   measuring the frequency shift of said focused and summed echo signals with respect to the emission frequency spectrum caused by blood flow in the sample volume, and deriving from the frequency shift the velocity of blood flow and displaying the flow velocity visually.

9. The method of claim 8 wherein the multiple impulse excitation of every selected array element is repeated at a preset but variable repetition frequency depending upon the magnitude of flow velocity and range to the sample volume.

10. The method of claim 9 wherein the number of impulses per variable repetition interval applied to each array element is constant, and wherein the variable repetition frequency is selected from the range of about 4 kilohertz to 16 kilohertz.

11. A duplex ultrasonic imaging system having a B-scan and Doppler orientation mode of operation and a subsequent Doppler mode of operation for blood flow velocity measurements comprising
   a common transducer array for both modes comprised of plural piezoelectric elements for transmitting pulses of ultrasound and generating received echo signals,
   means for single impulse excitation of selected array elements during B-scan operation to sequentially produce wide bandwidth ultrasound pulses with a preselected emission center frequency that are transmitted along different scan lines to perform a scan of a region being examined,
   means for amplifying and focusing and summing said echo signals, and means for displaying focused and summed echo signals as a visual image of the insonified region,
   means for multiple impulse excitation of selected array elements during Doppler operation ot sequentially produce narrow bandwidth ultrasound pulses that are transmitted along a chosen scan line intersecting a sample volume through which the velocity of blood flow is to be measured, said multiple impulses having a frequency approximately equal to said emission center frequency, the received echo signals amplified and focused and summed by the previously mentioned means,
   means for measuring the frequency shift of focused and summed echo signals with respect to the emission frequency spectrum caused by blood flow in the sample volume, and means for deriving the velocity of blood flow from the frequency shift and for displaying the flow velocity visually.

12. The duplex system of claim 11 wherein said means for single impulse excitation and means for multiple impulse excitation, whereby the bandwidth of the emitted ultrasound pulse is varied, is comprised by a common pulser means and controller therefor.

13. The duplex system of claim 11 or claim 12 wherein said means for multiple impulse excitation in Doppler mode generates multiple impulses for every selected array element with a variable repetition interval.

14. The duplex system of claim 11 or claim 12 wherein said means for multiple impulse excitation generates a constant number of impulses per repetition interval and wherein the repetition interval is variable depending upon the magnitude of flow velocity and range to the sample volume.

* * * * *